United States Patent [19]
Bessard et al.

[11] Patent Number: 5,840,892
[45] Date of Patent: Nov. 24, 1998

[54] PROCESS FOR THE PREPARATION OF SUBSTITUTED PYRIMIDINES

[75] Inventors: Yves Bessard, Sierre; Gerhard Stucky, Brig-Glis, both of Switzerland

[73] Assignee: Lonza AG, Gampel/Valais, Switzerland

[21] Appl. No.: 838,321

[22] Filed: Apr. 8, 1997

[30] Foreign Application Priority Data

Apr. 9, 1996 [CH] Switzerland .............................. 0893/96

[51] Int. Cl.$^6$ ...................... C07D 401/06; C07D 239/34; C07D 239/52
[52] U.S. Cl. ........................ 544/302; 544/300; 544/310; 544/313; 544/314; 544/317; 544/318
[58] Field of Search ...................................... 544/302, 300, 544/310, 313, 314, 317, 318

[56] References Cited

U.S. PATENT DOCUMENTS

| | | | |
|---|---|---|---|
| 5,270,289 | 12/1993 | Harde et al. | 544/314 |
| 5,318,945 | 6/1994 | Baumann et al. | 544/314 |
| 5,387,575 | 2/1995 | Harada et al. | 544/314 |

*Primary Examiner*—John M. Ford
*Attorney, Agent, or Firm*—Fisher, Christen & Sabol

[57] ABSTRACT

A novel process for the preparation of substituted pyrimidine derivatives of the general formula:

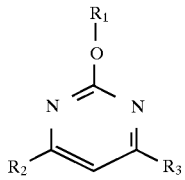

in which a halopyrimidine is reacted in the presence of a sulfinate with a compound selected from the series:

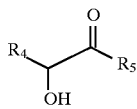

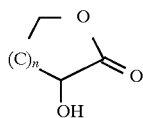

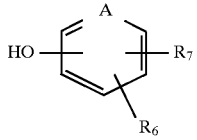

The compounds of the general formula I are precursors of, for example, compounds with herbicidal activity.

24 Claims, No Drawings

PROCESS FOR THE PREPARATION OF SUBSTITUTED PYRIMIDINES

BACKGROUND OF THE INVENTION

1. Field of the Invention

The invention relates to a novel process for the preparation of substituted pyrimidine derivatives of the general formula:

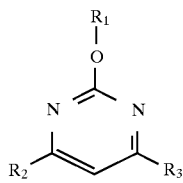

in which $R_1$, $R_2$ and $R_3$ have the meaning set out hereinafter.

The compounds of the general formula I are important precursors for the prepartion of, for example, active substances with herbicidal activity (compare European Published Patent Application No. A 0,562,510). The compounds of the general formula I may have an asymmetric carbon atom in the position adjacent to the carbonyl group in the substituent $R_1$. The following statements therefore embrace both the enantiomerically pure compounds and the racemates and any mixtures of the enantiomers with one another.

2. Background Art

Processes for the preparation of substituted pyrimidines of the general formula I are known. Thus, European Published Patent Application No. A 0,562,510 describes the preparation of, for example, methyl L-2-(4,6-dimethoxy-2-pyrimidinyloxy)-3-methylbutanoate by reaction of 2-benzylsulfonyl-4,6-dimethoxypyrimidine with L-α-hydroxyisovaleric acid in the presence of potassium carbonate. However, provision of the sulfonyl compound is difficult and elaborate and, as a rule, it must be prepared in several process steps starting from 2-thio-4,6-dimethoxypyrimidine.

Attempts were subsequently made to react 2-chloro-4,6-dimethoxypyrimidine directly with a hydroxyl compound. However, this reaction took place so slowly and incompletely that there was a need to look for a new way.

BROAD DESCRIPTION OF THE INVENTION

The main object of the invention is to provide a simple route, which can be carried out on the industrial scale, to the compounds of the general formula I. Other objects and advantages of the invention are set out herein or are obvious herefrom to one skilled in the art.

The invention involves a process for the preparation of substituted pyrimidine derivatives of the general formula:

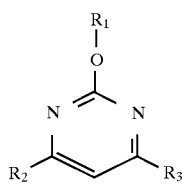

in which $R_1$ has the meaning of:

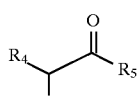

in which $R_4$ has the meaning of H, alkyl, aryl, arylalkyl, carboxyl, alkylcarbonyl or alkoxycarbonyl, and in which $R_5$ has the meaning of hydroxyl, alkoxy, aryloxy or alkyl,

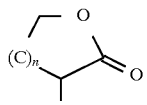

in which n has the meaning of 1 or 2,

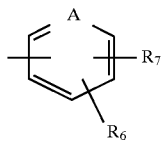

in which A has the meaning of CH or N and in which $R_6$ and $R_7$ are identical or different and each denotes hydrogen, alkyl, alkoxy, aryl, aryloxy or the group

—COOR$_8$ in which $R_8$ has the meaning of hydrogen, alkyl or aryl, and $R_2$ and $R_3$ are identical or different and each denotes H, alkyl, alkoxy, alkylthio, halogen, haloalkoxy, amino, alkylamino or dialkylamino, comprising reacting a halopyrimidine of the general formula:

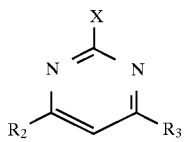

in which X denotes a halogen atom, and $R_2$ and $R_3$ have the meaning defined above, with a hydroxyl compound selected from the series:

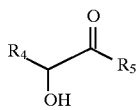

in which $R_4$ and $R_5$ have the meanings defined above,

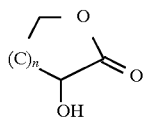

in which n has the meaning defined above,

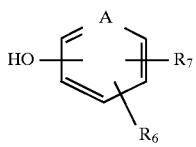

in which A, $R_6$ and $R_7$ have the meanings defined above, in the presence of a sulfinate of the general formula:

$R_9SO_2^- M^+$    IV in which $R_9$ denotes H, alkyl, aryl, arylalkyl or alkoxyaryl, and M denotes an alkali metal or alkaline earth metal atom, and in the presence of an inorganic or organic base to give the final product.

Preferably the reaction takes place in the presence of catalytic amounts of the sulfinate of the general formula IV.

Preferably the sulfinate of the general formula IV is employed in an amount of 1 to 25 mol percent based on the halopyrimidine of the general formula II employed. Preferably $M^+$ in the sulfinate of the general formula IV has the meaning of an alkali metal atom, selected from the series sodium, potassium and lithium, and $R_9$ has the meaning of $(C_1–C_4)$-alkyl, phenyl-$(C_1–C_4)$-alkyl or optionally $(C_1–C_4)$-alkyl-substituted phenyl.

Preferably an inorganic base is used. Preferably an alkali metal or alkaline earth metal carbonate is used as the inorganic base. Preferably the reaction is carried out in the presence of a polar solvent. Preferably the reaction temperature is chosen between 50° and 150° C.

Preferably the reaction is carried out in two stages in such a way that initially, in the first stage, the halopyrimidine of the general formula II is reacted in the presence of essentially stoichiometric amounts of sulfinate of the general formula IV and of an inorganic or organic base to give a sulfone of the general formula:

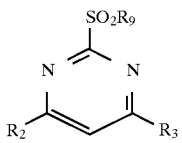

V in which $R_2$, $R_3$ and $R_9$ have the meanings defined above, and, in the second stage, the sulfone of the general formula V is converted with a hydroxyl compound selected from the series of compounds of the general formula IIIa, IIIb and IIIc, and in the presence of an inorganic or organic base into the final product of the general formula I. Preferably $M^+$ in the sulfinate of the general formula IV has the meaning of an alkali metal atom selected from the series sodium, potassium and lithium, and $R_9$ has the meaning of $(C_1–C_4)$-alkyl, phenyl-$(C_1–C_4)$-alkyl or optionally $(C_1–C_4)$-alkyl-substituted phenyl. Preferably an inorganic base is used. Preferably an alkali metal carbonate or an alkaline earth metal carbonate is used as the inorganic base. Preferably a polar solvent is present in the first stage and in the second stage. Preferably the reaction temperature chosen both for the first stage and for the second stage is between 50° and 150° C.

DETAILED DESCRIPTION OF THE INVENTION

The radicals indicated in the following general formulae I to V can have the following meanings:

Alkyl, either alone or as a constituent of alkoxy, alkylcarbonyl, alkoxycarbonyl, alkylthio, alkylamino, dialkylamino, haloalkoxy, arylalkyl or the like, can, in each case, be straight-chain or branched and expediently comprise 1 to 6 carbon atoms, preferably 1 to 4 carbon atoms. Those which can be literally mentioned are methyl, ethyl, n- or i-propyl, n-, i- or t-butyl, pentyl and its isomers or hexyl and its isomers.

Aryl expediently means an optionally substituted phenyl or naphthyl group, preferably a phenyl group. Arylalkyl consequently expediently represents phenyl-$(C_1–C_4)$-alkyl, in particular benzyl and aryloxy preferably represents phenoxy. Both alkyl and aryl can have one or more substituents, expediently from the series $(C_1–C_4)$-alkyl; halogen, for example fluorine or chlorine; $(C_1–C_4)$-haloalkyl, for example, trifluoromethyl; $(C_1–C_4)$-alkoxy, for example, methoxy or ethoxy; $(C_1–C_4)$-haloalkoxy, nitro or cyano.

Suitable halogens are fluorine, chlorine and bromine or iodine, in particular fluorine or chlorine. Correspondingly, haloalkoxy can represent, for example, trifluoromethoxy or trichloromethoxy.

According to the invention, the substituted pyrimidine derivatives of the general formula:

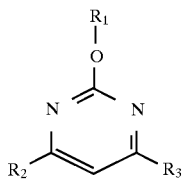

I in which $R_1$ has the meaning of:

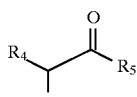

(i)

in which $R_4$ has the meaning of H, alkyl, aryl, arylalkyl, carboxyl, alkylcarbonyl or alkoxycarbonyl, and in which $R_5$ has the meaning of hydroxyl, alkoxy, aryloxy or alkyl,

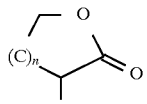

(ii)

in which n has the meaning of 1 or 2,

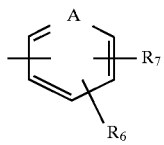

(iii)

in which A has the meaning of CH or N and in which $R_6$ and $R_7$ are identical or different and denote hydrogen, alkyl, alkoxy, aryl, aryloxy or a group

—COOR$_8$ in which $R_8$ has the meaning of hydrogen, alkyl or aryl, $R_2$ and $R_3$ are identical or different and denote H, alkyl, alkoxy, alkylthio, halogen, haloalkoxy, amino, alkylamino or dialkylamino, are prepared by reacting a halopyrimidine of the general formula:

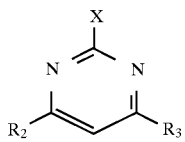

II in which X denotes a halogen atom, and $R_2$ and $R_3$ have the stated meaning, with a hydroxyl compound selected from the series:

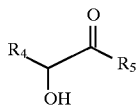

IIIa in which $R_4$ and $R_5$ have the meaning defined above,

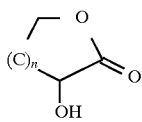 IIIb in which n has the meaning defined above,

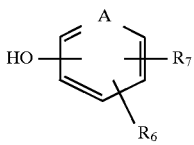 IIIc in which A, $R_6$ and $R_7$ have the meaning defined above, in the presence of a sulfinate of the general formula:

$$R_9SO_2^-M^+ \quad \text{IV}$$

in which $R_9$ denotes H, alkyl, aryl, arylalkyl or alkoxyaryl and M denotes an alkali metal or alkaline earth metal atom, and in the presence of an inorganic or organic base to give the final product.

The halopyrimidine of the general formula II as starting material of the process according to the invention can be provided in a simple manner and on the industrial scale by the process, for example, of European Published Patent Application No. A 0,582,288.

The hydroxyl compounds selected from the series of general formulae IIIa, IIIb, IIIc are, as a rule, commercially obtainable or can be prepared by conventional methods.

The hydroxyl compounds are expediently employed in stoichiometric amounts based on the halopyrimidine of the general formula II.

The reaction according to the invention can be carried out as a two-stage process or, preferably, as a so-called "one-pot synthesis".

In the preferred variant of the "one-pot synthesis", the sulfinate of the general formula IV is employed in catalytic amounts of, expediently, 1 to 25 mol percent, preferably 5 to 10 mol percent, based on the halopyrimidine of the general formula 11 employed.

The compounds expediently employed as sulfinates of the general formula IV are those in which $R_9$ has the meaning of ($C_1$–$C_4$) -alkyl, phenyl-($C_1$–$C_4$)-alkyl or optionally ($C_1$–$C_4$)-alkyl- or ($C_1$–$C_4$)-alkoxy-substituted phenyl. $R_9$ preferably has the meaning of methyl, p-methylphenyl, p-methoxyphenyl or benzyl. $M^+$ expediently has the meaning of an alkali metal atom selected from the series sodium, potassium and lithium, preferably of sodium. Preferred sulfinates are consequently sodium methanesulfinate, sodium p-toluenesulfinate or sodium benzylsulfinate.

The reaction according to the invention takes place in the presence of an inorganic or organic base. Suitable representatives of organic bases are tertiary amines, such as, triethylamine or diisopropylethylamine, which is known as Hünig's base.

On the other hand, it is preferred to use inorganic bases, such as, alkali metal or alkaline earth metal carbonates, in particular alkali metal carbonates, such as, potassium carbonate or sodium carbonate. The base is expediently employed in an amount of 1 mol equivalents to 3 mol equivalents, preferably of 1 mol equivalents to 1.5 mol equivalents, based on the halopyrimidine of the general formula II employed.

The reaction advantageously takes place in the presence of a polar solvent which is inert towards the reactants.

Solvents which have proved to be particularly suitable are N,N-dimethylformamide, sulfolane, dioxane, dimethyl sulfoxide or glycol ethers, such as, diglyme, but in particular N,N-dimethylformamide.

The reaction expediently takes place at a temperature between 50° and 150° C., preferably between 90° and 110° C., advantageously with substantial exclusion of water.

After a reaction time of approximately 0.5 to 24 hours, the final product of the general formula I can be isolated in good yields of up to 90 percent in a competent manner, for example, by extraction from the reaction mixture.

The reaction by the two-stage process differs from the preferred "one-pot variant" by taking place with essentially stoichiometric amounts of the sulfinate of the general formula IV.

In this process, the halopyrimidine of the general formula II is reacted in a first stage with the sulfinate of the general formula IV and in the presence of an inorganic or organic base initially to give a sulfone of the general formula:

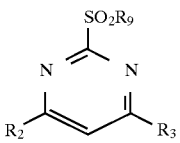 V in which $R_2$, $R_3$, and $R_9$ have the meanings defined above. This sulfone can be isolated from the reaction mixture in a manner customary to the skilled person, or else be employed directly for the second stage.

The reaction in the second stage then takes place with the hydroxyl compound selected from the series of compounds of the general formula IIIa, IIIb and IIIc in the presence of an inorganic or organic base to give the final product.

The choice of the base and of the reaction conditions for the two-stage process can be substantially based on the "one-pot process".

EXAMPLE 1

(two-stage process)

(a1) Preparation of 4,6-dimethoxy-2-(4-toluenesulfonyl) pyrimidine 4.38 g (25.0 mmol) of 2-chloro-4,6-dimethoxy-pyrimidine and 4.68 g (26.3 mmol) of sodium p-toluenesulfinate were heated in 25 ml of N,N-dimethylformamide to 100° C. while stirring. After 5 hours, the solvent was removed in a rotary evaporator at 60° C./20 mbar. The residue was taken up in 90 ml of water and 90 ml of ethyl acetate. After the organic phase had been separated off, the aqueous phase was again extracted with 75 ml of ethyl acetate. The combined organic phases was washed with water, dried over magnesium sulfate and evaporated. The residue was purified by chromatography on a silica gel column (eluent hexane/ethyl acetate 4:1). The title product was obtained from the product fraction in the form of a white powder in a yield of 3.79 g (15 percent of theory). The melting point of the title compound was 129.2° to 133.4° C. Other data concerning the title compound was:

$^1$H NMR (DMSO, MHz 400)δ=7.92 (2H, d); 7.50 (2 H, d); 6.48 (1 H, s); 3.87 (6 H, s); 2.43 (3 H, s). MS: 294 (MP), 279, 261, 209.

(a2) Preparation of 4,6-dimethoxy-2-methanesulfonylpyrimidine

The title product was prepared as in Example (a1) using sodium methanesulfinate.

(b1) Preparation of methyl (+/−)-2-(4,6-dimethoxy-2-pyrimidinyloxy)-3,3-dimethylbutanoate 2.94 g (10.0 mmol) of 4,6-dimethoxy-2-(p-toluenesulfonyl)pyrimidine and 1.55 g (10.5 mmol) of methyl (+/−)-2-hydroxy-3,3-dimethylbutanoate were heated in the presence of 2.07 g (15.0 mmol) of potassium carbonate in 20 ml of N,N-dimethylformamide to 100° C. with stirring. After 5 hours, the solvent was removed in a rotary evaporator at 60° C./20 mbar. The residue was taken up in 30 ml of water and 30 ml of dichloromethane. After the organic phase had been separated off, the aqueous phase was again extracted with 20 ml of dichloromethane. The combined organic phases were washed with water, dried over magnesium sulfate and evaporated. The title product was obtained in a yield of 2.30 g (80.9 percent of theory) in the form of yellowish crystals (GC content 100 percent).

(b2) Preparation of methyl (+/−)-2-(4,6-dimethoxy-2-pyrimidinyloxy)-3,3-dimethylbutanoate 2.18 g (10.0 mmol) of 4,6-dimethoxy-2-methylsulfonylpyrimidine and 1.62 g (11.0 mmol) of methyl (+/−)-2-hydroxy-3,3-dimethylbutanoate were heated in the presence of 2.07 g (15.0 mmol) of potassium carbonate in 20 ml of N,N-dimethylformamide to 60° with stirring. After 3 hours, the solvent was removed in a rotary evaporator at 60° C./20 mbar. The residue was taken up in 40 ml of water and 40 ml of ethyl acetate. After the organic phase had been separated off, the aqueous phase was again extracted with 40 ml of ethyl acetate. The combined organic phases was washed with water, dried over magnesium sulfate and evaporated. The title product was obtained in a yield of 2.76 g (93.8 percent of theory) in the form of pale yellowish crystals (GC content 96.6 percent).

EXAMPLE 2a (one-pot process)

Preparation of methyl (+/−)-2-(4,6-dimethoxy-2-pyrimidinyloxy)-3,3-dimethylbutanoate 4.38 g (25 mmol) of 2-chloro-4,6-dimethoxypyrimidine, 3.90 g (25 mmol) of methyl (+/−)-2-hydroxy-3,3-dimethylbutanoate and 0.66 g (6.3 mmol) of sodium methanesulfinate were heated in the presence of 5.17 g (37.5 mmol) of potassium carbonate in 25 ml of N,N-dimethylformamide to 120° C. with stirring. After 2 hours, the solvent was removed in a rotary evaporator at 70° C./20 mbar. The residue was taken up in 30 ml of water and 30 ml of dichloromethane. After the organic phase had been separated off, the aqueous phase was again extracted with 20 ml of dichloromethane. The combined organic phases was washed with water, dried over magnesium sulfate and evaporated. The title product was obtained in a yield of 5.93 g (82.7 percent of theory) in the form of pale yellowish crystals (GC content 99.2 percent). The melting point of the title compound was 104.4° to 107.0° C. Other data concerning the title compound was:

$^1$H NMR (DMSO, MHz 400)δ=5.88 (1 H, d); 4.70 (1 H, d); 3.85 (6 H, s); 3.65 (3 H, s); 1.07 (9 H, s). MS: 284 (MP); 269, 228, 196, 169, 157.

EXAMPLE 2b (one-pot process)

Preparation of methyl S-(+)-(4,6-dimethoxy-2-pyrimidinyloxy)-3,3-dimethylbutanoate.

1.75 g (10 mmol) of 2-chloro-4,6-dimethoxypyrimidine, 1.49 g (10 mmol) of methyl S-(+)-2-hydroxy-3,3-dimethylbutanoate and 0.45 g (2.5 mmol) of sodium p-toluenesulfinate were heated in the presence of 2.07 g (15 mmol) of potassium carbonate in 10 ml of N,N-dimethylformamide to 120° C. with stirring. After 7 hours, the solvent was removed in a rotary evaporator at 60° C./20 mbar. The residue was taken up in 30 ml of water and 30 ml of dichloromethane. After the organic phase had been separated off, the aqueous phase was again extracted with 20 ml of dichloromethane. The combined organic phases was washed with water, dried over magnesium sulfate and evaporated. The residue was purified by chromatography on a silica gel column (eluent hexane/ethyl acetate 4:1). The title product was obtained from the product fraction in the form of pale yellowish crystals in a yield of 1.6 g (56.3 percent of theory) (GC content 99 percent). The melting point of the title product was 111.4° to 114.8° C. Other data concerning the title product was:

S/R enantiomer ratio=96.7/3.3

$^1$H NMR (DMSO, MHz 400)δ=5.88 (1 H, s); 4.70 (1 H, s); 3.82 (6 H, s); 3.65 (3 H, s); 1.04 (9 H, s).

EXAMPLE 2c (one-pot process)

Comparison Without Addition of Sulfinate

Preparation of methyl (+/−)-2-(4,6-dimethoxy-2-pyrimidinyloxy)-3,3-dimethylbutanoate The reaction was carried our as in Example 2a but without addition of sodium sulfinate. The conversion of precursor reached after a reaction time of 24 hours was 54 percent.

EXAMPLE 3

(one-pot process)

Preparation of (+/−)-3-(4,6-dimethoxy-2-pyrimidinyloxy)-2-butanone 4.38 g (25 mmol) of 2-chloro-4,6-dimethoxypyrimidine, 2.31 g (26.2 mmol) of 3-hydroxy-2-oxobutane and 0.66 g (6.3 mmol) of sodium methanesulfinate were heated in the presence of 5.17 g (37.5 mmol) of potassium carbonate in 25 ml of N,N-dimethylformamide to 120° C. with stirring. After 3 hours, the solvent was removed in a rotary evaporator at 70° C./20 mbar. The residue was purified by chromatography on a silica gel column (eluent hexane/ethyl acetate 4:1). The title product was obtained from the product fraction in the form of a pale yellowish oil in a yield of 4.58 g (80.4 percent of theory) (GC content 99 percent). Other data concerning the title compound was:

$^1$H NMR (DMSO, MHz 400)δ=5.87 (1 H, s); 5.70 (1 H, q); 3.82 (6 H, s); 2.25 (3 H, s); 1.44 (3 H, d). MS: 226; 211; 183; 157; 139

EXAMPLE 4

(one-pot process)

Preparation of (+/−)-3-(4,6-dimethoxy-2-pyrimidinyloxy)-2-dihydrofuranone 1.75 g (10 mmol) of 2-chloro-4,6-dimethoxypyrimidine, 1.02 g (10 mmol) of α-hydroxy-γ-butyrolactone and 0.26 g (2.5 mmol) of sodium methanesulfinate were heated in the presence of 2.07 g (15.0 mmol) of potassium carbonate in 10 ml of N,N-dimethylformamide to 120° C. with stirring. After 2 hours, the solvent was removed in a rotary evaporator at 70° C./20 mbar. The residue was taken up in 30 ml of water and 30 ml of dichloromethane. After the organic phase had been separated off, the aqueous phase was again extracted with 20 ml of dichloromethane. The combined organic phases was washed with water, dried over magnesium sulfate and evaporated. The title product was obtained in a yield of 0.43 g (15.5 percent of theory) in the form of a pale brown oil (GC content 94 percent). Other data concerning the title compound was:
MS: 240; 210; 181; 157.

EXAMPLE 5

(one-pot process)
Preparation of methyl 2-(4,6-dimethoxy-2-pyrimidinyloxy)-3-methylbenzoate 4.38 g (25 mmol) of 2-chloro-4,6-dimethoxypyrimidine, 4.17 g (25.0 mmol) of methyl 2-hydroxy-3-methylbenzoate and 0.66 g (6.3 mmol) of sodium methanesulfinate were heated in the presence of 5.17 g (37.5 mmol) of potassium carbonate in 25 ml of N,N-dimethylformamide to 120° C. with stirring. After 8 hours, the solvent was removed in a rotary evaporator at 60° C./20 mbar. The residue was taken up in 30 ml of water and 30 ml of dichloromethane. After the organic phase had been separated off, the aqueous phase was again extracted with 20 ml of dichloromethane. The combined organic phases was washed with water, dried over magnesium sulfate and evaporated. The residue was purified by chromatography on a silica gel column (eluent hexane/ethyl acetate 4:1). The title product was obtained from the product fraction in a yield of 5.23 g (65.8 percent of theory) (GC content 96 percent). The melting point of the compound was 73.8° to 79.1° C. Other data concerning the title compound was:
$^1$H NMR (DMSO, MHz 400)δ=7.75 (1 H, d); 7.58 (1 H, d); 7.30 (1 H, t); 5.95 (1 H, s); 3.75 (6 H, s); 3.62 (3 H, s); 2.17 (3 H, s). GC/MS: 304; 273, 245

EXAMPLE 6

(one-pot process)
Preparation of methyl 2-(4,6-dimethoxy-2-pyrimidinyloxy) benzoate 4.38 g (25 mmol) of 2-chloro-4,6-dimethoxypyrimidine, 3.80 g (25.0 mmol) of methyl 2-hydroxybenzoate and 0.66 g (6.3 mmol) of sodium methanesulfinate were heated in the presence of 5.17 g (37.5 mmol) of potassium carbonate in 25 ml of N,N-dimethylformamide to 120° C. with stirring. After 1.5 hours, the solvent was removed in a rotary evaporator at 60° C./20 mbar. The residue was taken up in 30 ml of water and 30 ml of dichloromethane. After the organic phase had been separated off, the aqueous phase was again extracted with 20 ml of dichloromethane. The combined organic phases was washed with water, dried over magnesium sulfate and evaporated. The residue was purified by chromatography on a silica gel column (eluent hexane/ethyl acetate 4:1). The title product was obtained from the product fraction in a yield of 5.76 g (77.0 percent of theory) (GC content 97 percent). The melting point of the title compound was 106.7° C. to 108.3° C. Other data concerning the title compound was:
$^1$H NMR (DMSO, MHz 400)δ=7.92 (1 H, d); 7.70 (1 H, t); 7.40 (1 H, t); 7.32 (1 H, d); 5.95 (1 H, s); 3.75 (6 H, s); 3.62 (3 H, s). GC/MS: 290; 231.

EXAMPLE 7

(one-pot process)
Preparation of methyl 3-(4,6-dimethoxy-2-pyrimidinyloxy)-2-pyridinecarboxylate 1.75 g (10 mmol) of 2-chloro-4,6-dimethoxypyrimidine, 1.53 g (10 mmol) of methyl 3-hydroxy-2-pyridinecarboxylate and 0.104 g (1.0 mmol) of sodium methanesulfinate were heated in the presence of 2.17 g (15 mmol) of potassium carbonate in 6 ml of N,N-dimethylformamide to 100° C. with stirring. After 5 hours, the solvent was removed in a rotary evaporator at 60° C./20 mbar. The residue was purified by chromatography on a silica gel column (eluent hexane/ethyl acetate 4:1). The title product was obtained from the product fraction in the form of a yellowish oil in a yield of 1.94 g (61 percent of theory) (GC content 92.3 percent). Other data concerning the title compound was:
$^1$H NMR (DMSO, MHz 400)δ=8.58 (1 H, d); 7.90 (1 H, d); 7.74 (1 H, dd); 6.01 (1 H, s); 3.75 (6 H, s); 3.68 (3 H, s).

What is claimed is:

1. A process for the preparation of a substituted pyrimidine derivative of formula:

$$\begin{array}{c} R_1 \\ | \\ O \\ N \diagup \diagdown N \\ R_2 \diagdown \diagup R_3 \end{array} \quad \text{I}$$

wherein $R_1$ is:

$$R_4 \underset{}{\overset{O}{\diagup\!\!\diagdown}} R_5 \qquad (i)$$

wherein $R_4$ is a member of the group consisting of H, alkyl, aryl, arylalkyl, carboxyl, alkylcarbonyl and alkoxycarbonyl, and wherein $R_5$ is a member selected from the group consisting of hydroxyl, alkoxy, aryloxy and alkyl, $$(C)_n \underset{}{\overset{O}{\diagup\!\!\diagdown}} O \qquad (ii)$$

wherein n is 1 or 2, (iii) [ring structure with A, $R_6$, $R_7$]

wherein A is CH or N and wherein $R_6$ and $R_7$ are identical or different and each is a member selected from the group consisting of hydrogen, alkyl, alkoxy, aryl, aryloxy and group

—COOR$_8$ wherein $R_8$ is hydrogen, alkyl or aryl, and $R_2$ and $R_3$ are identical or different and each is a member selected from the group consisting of H, alkyl, alkoxy, alkylthio, halogen, haloalkoxy, amino, alkylamino and dialkylamino, comprising reacting a halopyrimidine of formula:

$$\begin{array}{c} X \\ | \\ N \diagup \diagdown N \\ R_2 \diagdown \diagup R_3 \end{array} \quad \text{II}$$

wherein X is a halogen atom, and $R_2$ and $R_3$ have the stated meanings, is reacted with a hydroxyl compound selected from the series:

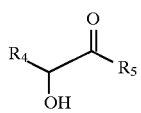

wherein $R_4$ and $R_5$ have the stated meanings,

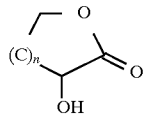

wherein n has the stated meaning,

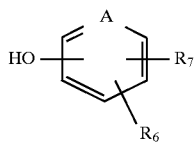

wherein A, $R_6$ and $R_7$ have the stated meanings, in the presence of a catalytic amount of a sulfinate of formula:

$$R_9SO_2^- M^+ \qquad \text{IV}$$

wherein $R_9$ is a member selected from the group consisting of H, alkyl, aryl, arylalkyl and alkoxyaryl, and M is an alkali metal or alkaline earth metal atom, and in the presence of an inorganic or organic base to give the final product.

2. The process according to claim 1, wherein the reaction takes place in the presence of catalytic amounts of the sulfinate of formula IV.

3. The process according to claim 2, wherein the sulfinate of formula IV is employed in an amount of 1 to 25 mol percent based on the halopyrimidine of formula II employed.

4. The process according to claim 3, wherein $M^+$ in the sulfinate of formula IV is an alkali metal atom which is selected from the group consisting of sodium, potassium and lithium, and $R_9$ is $(C_1-C_4)$-alkyl, phenyl-$(C_1-C_4)$-alkyl or optionally $(C_1-C_4)$-alkyl-substituted phenyl.

5. The process according to claim 4, wherein an inorganic base is used.

6. The process according to claim 5, wherein an alkali metal or alkaline earth metal carbonate is used an the inorganic base.

7. The process according to claim 6, wherein the reaction is carried out in the presence of a polar solvent.

8. The process according to claim 7, wherein the reaction temperature is chosen between 50° and 150° C.

9. The process according to claim 8, wherein $M^+$ in the sulfinate of formula IV is an alkali metal atom selected from the group consisting of sodium, potassium and lithium, and $R_9$ is $(C_1-C_4)$-alkyl, phenyl-$(C_1-C_4)$-alkyl or optionally $(C_1-C_4)$-alkyl-substituted phenyl.

10. The process according to any of claim 9, wherein an inorganic base is used.

11. The process according to claim 10, wherein an alkali metal carbonate or an alkaline earth metal carbonate is used as the inorganic base.

12. The process according to claim 11, wherein a polar solvent is present both in the first stage and in the second stage.

13. The process according to claim 12, wherein the reaction temperature chosen both for the first stage and for the second stage is between 50° and 150° C.

14. The process according to claim 1, wherein the sulfinate of formula IV is employed in an amount of 1 to 25 mol percent based on the halopyrimidine of formula II employed.

15. The process according to claim 1, wherein $M^+$ in the sulfinate of formula IV is an alkali metal atom which is selected from the group consisting of sodium, potassium and lithium, and $R_9$ is $(C_1-C_4)$-alkyl, phenyl-$(C_1-C_4)$-alkyl or optionally $(C_1-C_4)$-alkyl-substituted phenyl.

16. The process according to claim 1, wherein an inorganic base is used.

17. The process according to claim 16, wherein an alkali metal or alkaline earth metal carbonate is used as the inorganic base.

18. The process according to claim 1, wherein the reaction is carried out in the presence of a polar solvent.

19. The process according to claim 1, wherein the reaction temperature is chosen between 50° and 150° C.

20. A process for the preparation of a substituted pyrimidine derivative of formula:

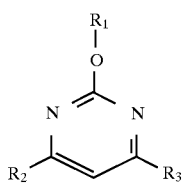

wherein $R_1$ is:

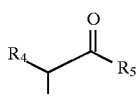

wherein $R_4$ is a member of the group consisting of H, alkyl, aryl, arylalkyl, carboxyl, alkylcarbonyl and alkoxycarbonyl, and wherein $R_5$ is a member selected from the group consisting of hydroxyl, alkoxy, aryloxy and alkyl,

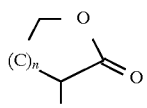

wherein n is 1 or 2,

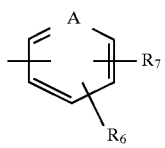

wherein A is CH or N and wherein $R_6$ and $R_7$ are identical or different and each is a member selected from the group consisting of hydrogen, alkyl, alkoxy, aryl, aryloxy and group

—COOR$_8$ wherein $R_8$ is hydrogen, alkyl or aryl, and $R_2$ and $R_3$ are identical or different and each is a member selected from the group consisting of H, alkyl, alkoxy, alkylthio, halo, haloalkoxy, amino, alkylamino and dialkylamino, comprising, initially, in a first step, reacting a halopyrimidine of formula:

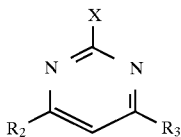

wherein X is a halogen atom, and $R_2$ and $R_3$ have the above-stated meanings, in the presence of essentially a stoichiometric amount of a sulfinate of formula:

$$R_9SO_2^-M^+ \qquad \text{IV}$$

wherein $R_9$ is a member selected from the group consisting of H, alkyl, aryl, arylalkyl and alkoxyaryl, and M is an alkali metal or alkaline earth metal atom, and in the presence of an inorganic or organic base to give a sulfone of formula:

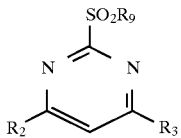

wherein $R_2$, $R_3$ and $R_9$ have the above-stated meanings, and, in a second stage, said sulfone of formula V is converted with a hydroxyl compound selected from the group consisting of:

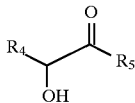

wherein $R_4$ and $R_5$ have the above-stated meanings,

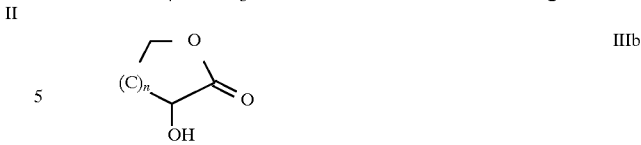

wherein n has the above-stated meaning,

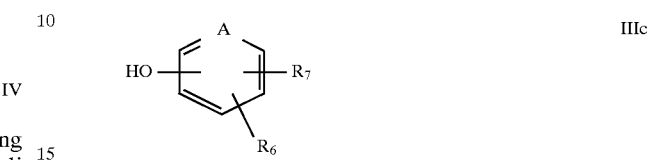

wherein A, $R_6$ and $R_7$ have the stated meanings, in the presence of an inorganic or organic base into said substituted pyrimidine derivative of formula I.

21. The process according to claim 20, wherein an inorganic base is used.

22. The process according to claim 21, wherein an alkali metal carbonate or an alkaline earth metal carbonate is used as the inorganic base.

23. The process according to claim 20, wherein a polar solvent is present both in the first stage and in the second stage.

24. The process according to claim 20, wherein the reaction temperature chosen both for the first stage and for the second stage is between 50° and 150° C.

* * * * *